United States Patent [19]
Feldman

[11] Patent Number: 5,342,194
[45] Date of Patent: Aug. 30, 1994

[54] DENTAL IMAGING MATRIX BAND FOR MAKING OR SETTING CROWNS AND BRIDGES ON PREPARED TEETH

[76] Inventor: Richard L. Feldman, 11 Wintergreen Dr., Easton, Conn. 06612

[21] Appl. No.: 67,819

[22] Filed: May 27, 1993

Related U.S. Application Data

[63] Continuation-in-part of Ser. No. 893,061, Jun. 3, 1992, Pat. No. 5,248,258.

[51] Int. Cl.5 ............................................... A61C 5/04
[52] U.S. Cl. ....................................... 433/39; 433/229
[58] Field of Search .............. 433/39, 40, 213, 229, 433/223

[56] References Cited

U.S. PATENT DOCUMENTS

| | | | |
|---|---|---|---|
| 3,921,299 | 11/1975 | Lazarus | 433/39 |
| 4,575,805 | 3/1986 | Moermann et al. | 433/223 |
| 4,837,732 | 6/1989 | Brandestini et al. | 433/223 |

*Primary Examiner*—Cary E. O'Connor
*Attorney, Agent, or Firm*—Arthur T. Fattibene; Paul A. Fattibene

[57] ABSTRACT

This disclosure is directed to a dental imaging matrix band for making a dental prosthetic restoration such as a ¾ crown, full crown, or fixed bridge with the use of a CAD-CAM machine. This is attained by encircling a tooth or teeth prepared for receiving the prosthetic restoration by an imaging matrix band having an actual enlarged beaded peripheral edge or an illusion of an enlarged beaded portion which can be optically read by a scanner of a CAD-CAM machine. The optical image of the tooth or teeth encircled by such an imaging matrix band is transformed by the CAD-CAM machine into a signal which controls the operation of the forming or milling portion of the CAD-CAM machine to shape a block of dental material into the shape of a prosthetic restoration to be fitted to the prepared tooth or teeth in accordance with the optical image of the prepared tooth or teeth. The matrix band is defined by a strip of thin non-reflective metallic material having a longitudinal edge thereof defining an enlarged bead or a thickened buccal and lingula side portions which can be optically scanned by a CAD-CAM machine; the image of which being transformed into a signal enabling the CAD-CAM to machine a prosthetic restoration to be received by the prepared tooth or teeth. In another form, the matrix band is formed of a uniform thickness which extends beyond the surface of the tooth and which is tapered outwardly to define an optical illusion simulating a thicker occlusal end which can be read by the CAD-CAM machine.

16 Claims, 2 Drawing Sheets

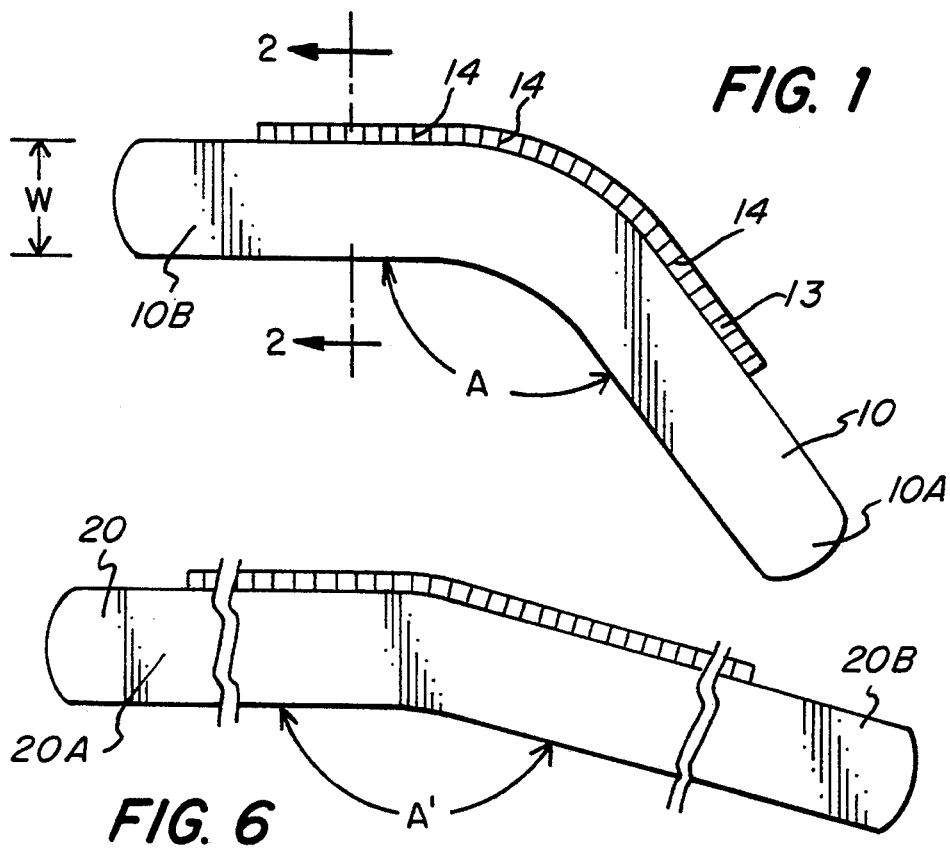
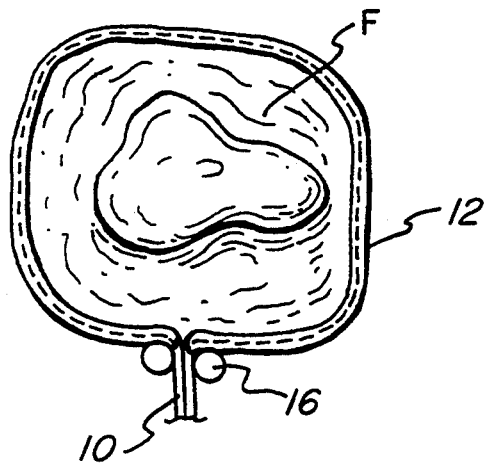
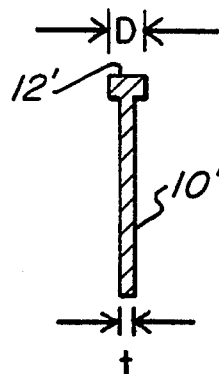
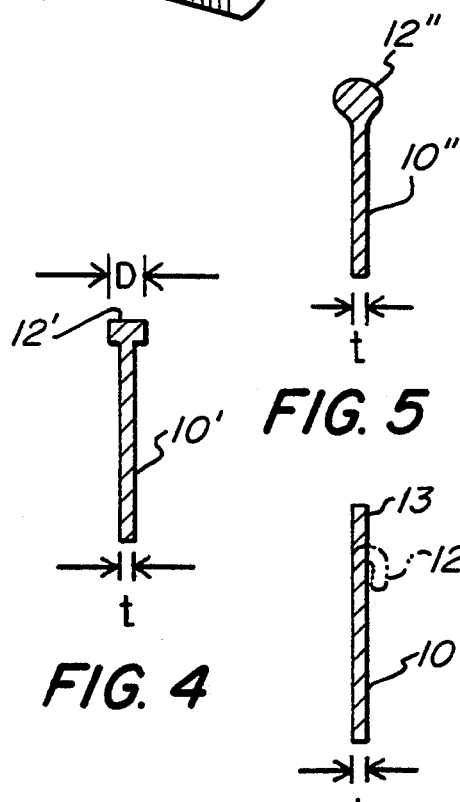
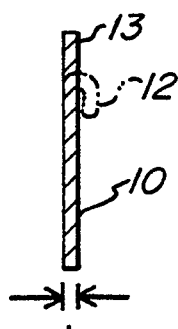

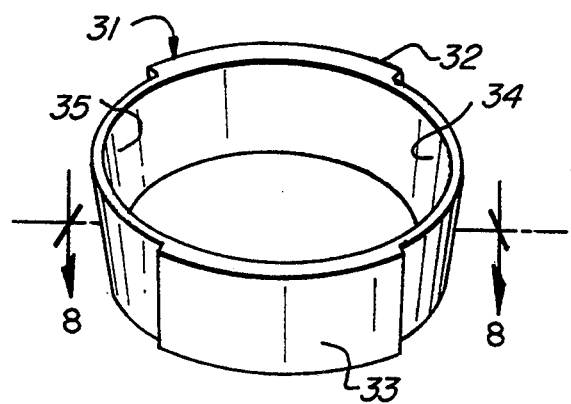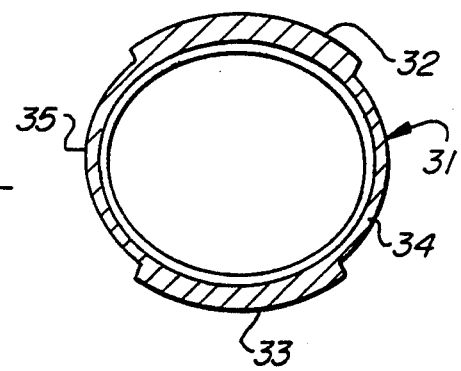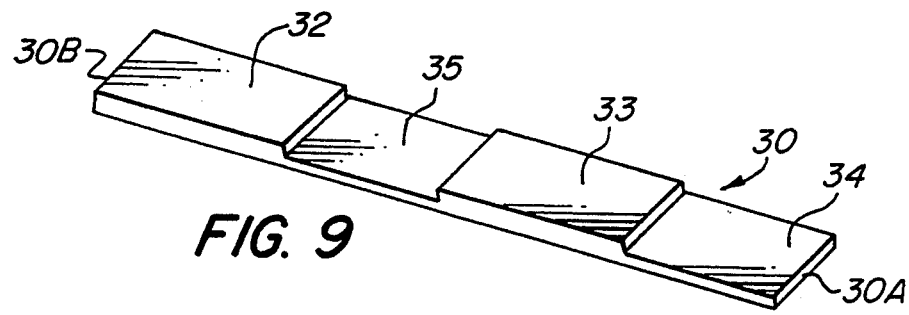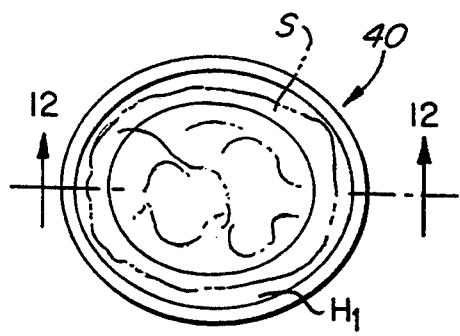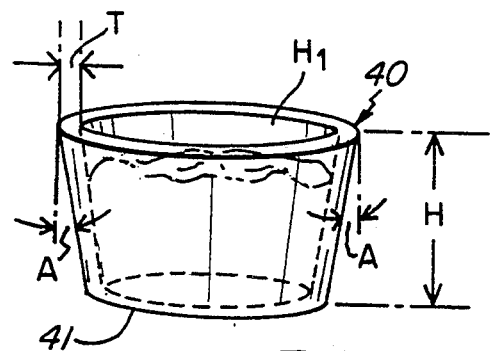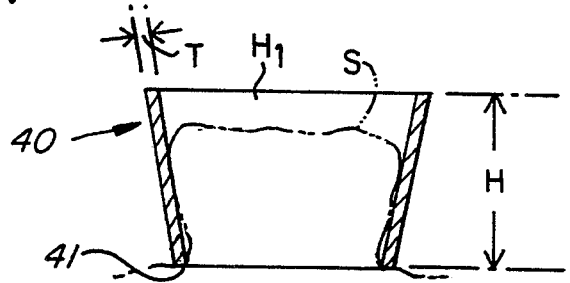

DENTAL IMAGING MATRIX BAND FOR MAKING OR SETTING CROWNS AND BRIDGES ON PREPARED TEETH

RELATED APPLICATIONS

This is a continuation-in-part application of my co-pending application Ser. No. 07/893,061 filed Jun. 3, 1992 for Dental Imaging Matrix Band and Method for Making or Setting Crowns and Bridges on Prepared Teeth, now U.S. Pat. No. 5,218,258, the latter relating to Disclosure Document No. 304,923 filed Mar. 31, 1992.

FIELD OF INVENTION

This invention is directed to a dental imaging matrix band for facilitating the making of crowns and bridges in conjunction with a CAD-CAM machine such as a SIEMENS CEREC.

PRIOR ART

Prior to this invention, dentists have utilized a CAD-CAM machine for making various types of restorative inlays, onlays and porcelain laminates for teeth. A CAD-CAM machine is a device which records an optical image of a tooth which has been prepared for an inlay, onlay or porcelain laminate, and which image is thereafter transformed into a signal transmitted to a forming wheel to machine or mill a block of ceramic material into the shape of the inlay, onlay or porcelain laminate to be placed in or on the prepared tooth in accordance with the optical image perceived by the CAD-CAM machine. The benefit of utilizing the CAD-CAM technique for making inlays, onlays or porcelain laminates is to eliminate the tedious and time consuming task of taking a traditional impression of the prepared tooth and thereafter sending the impression to a laboratory for making the final inlay, onlay or porcelain laminate. Not only is the laboratory work tedious and time consuming, it has the further disadvantage that such tooth restorations could not generally be completed in a single visit, thereby requiring the dentist to provide the patient with a temporary restoration and requiring the patient to return for another visit or treatment after the lab work has been completed.

A noted deficiency of the known CAD-CAM machines is that they are incapable of being used to make a ¾ crown, a full crown restoration or a fixed bridge. This is because the prepared tooth for a ¾ crown, a full crown or a fixed bridge cannot be imaged by the CAD-CAM machines whereby a proper signal can be transmitted to the forming wheel to machine or mill the ceramic block for making the required crown or bridge.

SUMMARY OF THE INVENTION

According to the present invention, the foregoing noted deficiency of the CAD-CAM type machines for making dental restorations is obviated by a specifically constructed matrix band which is adapted to be fitted to the prepared tooth for receiving the full or partial crown restoration or fixed bridge. The matrix band is constructed so as to enable the CAD-CAM machine to simulate an optical image of the outer periphery of the prepared tooth or area in a manner such that a proper signal can be transmitted to the milling portion of the machine to mill a full or partial crown or fixed bridge in accordance with the shape of the optical image defined by the matrix band. The matrix band is formed as a narrow blank of sheet material, e.g. a thin gauge flexible metallic strip which is non-reflective. Along the upper encircling portion of the band, there is provided a beaded edge to define or simulate the optical peripheral portion of the tooth or area to receive the full or partial crown or fixed bridge. The beaded edge can be formed by forming the beaded portion as an integral part of the band. The beaded edge may also be formed by providing a marginal flap or extension which can be readily reversely folded to define an optical visual edge adapted to be read by the optical scanner of the CAD-CAM machine. The opposed edges of the band are retained by a conventional band holder.

In another form of the invention, the matrix band comprises a metallic endless band which tapers slightly inwardly toward the gum line and which is arranged to be fitted to the prepared tooth. The matrix band is in the shape of a funnel and having a taper ranging between 7 to 12 degrees with the gingival end being the smaller diameter of approximately 6 mm and with the occlusal end being of a larger diameter of approximately 13 mm. The opposed lingual and buccal sides of the matrix band are provided with a thicker portion which is greater than the thickness forming the ends of the band that connect the lingual and buccal sides. This thickness is a lip that simulates the cavosurface margin of the tooth.

In still another form of the invention, the matrix band may comprise an endless, non-reflective metallic band having a uniform thickness which tapers inwardly toward the gum line or gingival end; and having a height which extends above the surface of the prepared tooth. Preferably, the matrix band has a uniform thickness of 0.2 mm; and having a taper ranging between 7 to 12 degrees. The arrangement is such that when the matrix band is applied to the tooth, the inclination of the matrix band extending above the prepared tooth, together with the thickness of the matrix band material simulates an optical image of the outer periphery of the prepared tooth or area in a manner such that a proper signal can be transmitted to the milling portion of the CAD-CAM machine to mill a crown or bridge in accordance to the shape of the optical image defined by the matrix band.

IN THE DRAWINGS

FIG. 1 is a side view of a matrix band embodying the invention adapted to form a full or partial crown.

FIG. 2 is a sectional view taken along line 2—2 of FIG. 1 wherein the dotted line shown illustrates the reversely folded position of the marginal flange to define the beaded edge.

FIG. 3 is a plan or top view of the matrix band of FIG. 2 disposed in encircling position about a prepared tooth.

FIG. 4 illustrates a sectional view of a modified embodiment.

FIG. 5 is a sectional view of another modified embodiment.

FIG. 6 is a side view of a matrix band embodying the invention for making a fixed bridge restoration.

FIG. 7 is a perspective view of a modified matrix band embodying the invention.

FIG. 8 is a section view taken along line 8—8 on FIG. 7.

FIG. 9 is a perspective expanded view of the matrix band of FIG. 7.

FIG. 10 is a perspective view of another modified embodiment.

FIG. 11 is a plan view of FIG. 10.

FIG. 12 is a section view taken along line 12—12 on FIG. 11.

DETAIL DESCRIPTION

This invention is directed to a method and device for making a prosthetic tooth restoration in the form of crowns, partial crowns or fixed bridges with the use of a CAD-CAM machine.

Referring to the drawings, FIG. 1 illustrates a side view of a metallic blank 10 from which the matrix band embodying the invention is formed. As shown, the blank 10 comprises a flat elongated blank or strip having angularly disposed sections 10A and 10B. The included angle A between sections 10A and 10B preferably falls in a range of 120 degrees to 140 degrees with a 130 degree angle being considered the optimal angle for making, e.g. a full or partial ¾ crown. For a bridge matrix band as shown in FIG. 6, the length of the band is made longer than that required for the crown matrix band of FIG. 1, as the bridge matrix band is required to encircle two or more teeth. The fixed bridge matrix band 20 as illustrated in FIG. 6 is provided with portions 20A and 20B which are longer than that of the crown matrix band 10 of FIG. 1 so that the band 20 may encircle two or more teeth. Also, the angle A is in the range of 160 degrees to 180 degrees with a preferred angle of 170 degrees. In all other respects, the construction is similar to that herein described. There must be an angle A, as shown in FIGS. 1 and 6, to allow the gingival edge of the band to tightly contact the tooth, diverging occlusally. This allows the optical impression to clearly see the floor F or "bottom line" of the tooth. The width "w" of the matrix blank is approximately 6 millimeters for a premolar tooth and 10 mm for a molar or an incisor tooth, or generally equal to the height of the tooth to be restored, which extends above the gum line.

According to this invention, the encircling portion of the band or blank 10, adapted to circumscribe the tooth or teeth which have been prepared to receive either a ¾ crown, a full crown or fixed bridge, is provided with an upper beaded edge 12. In the form of the invention shown in FIGS. 1 and 2, the beaded edge 12 of the matrix band 10 is defined by a marginal flap or extension 13 which is adapted to be reversely folded to define the beaded edge 12 as best seen in FIG. 2 in the dotted line showing. To facilitate the reverse folding of the marginal flap 13, a series of radial slits 14 may be longitudinally spaced along the marginal flap 13. The upper edge or beaded edge 12 of the band is shaped to define or approximate the upper peripheral contour of the tooth to be restored to form the basis of the signal transmitted to the milling portion of the CAD-CAM machine. Preferably, the width of the flap 13 which extends beyond the edge of the blank 10 is approximately 0.2 millimeters. By reversely folding the flap 13 to overlie the thickness of the band 10, the thickness of the beaded edge so formed of the band encircling the prepared tooth is more than doubled. This thickened edge of the band enables the optical scanner to accurately see the simulated periphery of the tooth which is translated into a signal that indicates the height or Z axis of the ¾ crown, full crown or fixed bridge to be milled by the CAD-CAM machine.

The thickness "t" of the blank 10, as illustrated in FIG. 2, is approximately 0.03 to 0.04 millimeters. By the reverse fold of the marginal flap 13, the thickness of the upper or beaded edge 12 is more than doubled.

FIG. 4 illustrates a further embodiment of the invention. In this form of the invention, the upper beaded edge 12' of the band 10' is formed as an integrally formed cross-head portion wherein the cross section of the blank 10' is "T" shaped. In all other respects, the band 10' is similar to that hereinbefore described.

FIG. 5 illustrates another modified embodiment. In this form of the invention, the beaded portion 12" of matrix band 10" is defined as rounded or circular beaded portion. If desired, the beaded edge 12' or 12" may comprise a separate member which is tack welded or otherwise secured or connected to the band or strip 10 or 10'.

In use, the matrix band 10, 10' or 10" of FIGS. 2, 4 or 5 respectively, is disposed about the tooth which has been prepared for receiving the partial or full crown as shown in FIG. 3, wherein the beaded edge 12, 12', 12" defines the upper periphery of the tooth to be restored. It will be understood that the free ends of the band are held together by a conventional matrix band holder, e.g. a Tofflemine holder 16. With the matrix band 10, 10', 10" in place as shown in FIG. 3, the optical scanner of the CAD-CAM machine is placed over the tooth to transmit the optical image to the screen of the CAD-CAM. The angle A of the matrix band provides an intimate, tight fit to the tooth gingivally and diverges away from the bottom or floor of the prepared tooth, allowing for a clear optical image of the floor of the tooth. The thickened beaded occlusal edge of the band simulates the walls of a tooth, creating an optical illusion or false cavosurface margin. Through the internal working of the CAD-CAM, the optical image perceived is transformed into a series of digital signals which allows the milling portion of the machine to mill an accurate ¾ crown, full crown or fixed bridge which is approximately shaped for application to the prepared tooth or teeth and to fit inside the simulated cavosurface margins created by the matrix band. The improved matrix band of this invention thus permits a dentist to utilize the CAD-CAM for making ¾ crowns, full crowns or fixed bridges simply and quickly, whereby the ¾ crown, full crown or fixed bridge is made and installed in a single sitting and without resorting to the heretofore tedious and time consuming traditional laboratory work. Thus, the dentist can now prepare a tooth for receiving a ¾ crown, a full crown or bridge, make the computer generated restoration, install and finish the same all in a single sitting.

To insure forming an accurate optical image, it is preferred that the material of the band be non-reflective. This can be attained by roughing the surface of the band to reduce shine or reflection.

After the ¾ crown, full crown or fixed bridge has been milled to fit the shape of the prepared tooth and inside the simulated cavosurface margin created by the matrix band in accordance with the optical image made possible by the matrix band, the crown is polished and finished to harmonize with the patient's natural teeth.

FIGS. 7 to 9 illustrate a further embodiment of an imaging matrix band. As shown in FIG. 9, the imaging matrix band is illustrated as an elongated blank or strip of a metallic material 30, e.g. copper, aluminum, or the like, having a length sufficient to encircle at least one prepared tooth to be imaged and restored. As shown, the blank 30 is provided with opposed ends 30A, 30B arranged to be suitably joined, e.g. by soldering, fusing, bonding, molding or pressing and the like, to define an endless band 31 as shown in FIGS. 7 and 8. In this form of the invention, the endless band or loop 31, as formed in FIGS. 7 and 8, is arranged to taper slightly inwardly toward the gum line as best seen in FIG. 7. The endless loop or band 31 is formed so that the portion of the loop or band defining the buccal side 32 and opposed lingual side 33 are made thicker than the opposed mesial and distal ends 34 and 35 of the band or loop 31. The thickened portion defines a means which is formed integral with the band which will simulate a clear optical image of the floor of the tooth when the imaging matrix band described is being used. The arrangement is such that the thinner opposed ends 34, 35 of the endless band can be fitted between adjacent teeth so as to circumscribe the prepared area or tooth; with the thickened sides 32, 33 defining the buccal and lingual surfaces of the prepared area or tooth which is to be optically imaged. As best seen in FIGS. 7 and 8, the thickened buccal and lingual sides 32 and 33 are disposed on the external portion of the matrix band when applied to a prepared tooth. This arrangement provides for a smooth internal surface of the matrix band so as to enable the band to be snugly tightened about the prepared tooth. As hereinbefore described, the metallic strip 30 is rendered non-reflective by roughing the surface to reduce reflection. In all other respects, the matrix band 31 is used in a manner hereinbefore described with respect to FIGS. 1 to 6.

FIGS. 10 to 12 illustrate a further embodiment of an imaging matrix band 40 embodying the present invention. As best seen in FIGS. 10 and 11, the imaging matrix band 40 comprises an endless band of a non-reflective material, e.g. copper, aluminum or the like, having a uniform thickness "T" of approximately 0.2 mm. The endless band 40 is formed with a diameter sufficient to encircle at least one prepared tooth. It will be understood that the endless band 40 can be formed as a continuous band, or may be formed as an elongated band which may be wrapped about the tooth to be restored and held in place by a conventional matrix band holder, e.g. a Tofflemine holder 16, as shown in FIG. 3. The continuous band 40 can either be formed as a continuous tube which may be sectioned to a desired height dimension for a particular size matrix band, or may be formed from elongated flat strips, the opposed ends of which may be joined as by soldering, fusing, bonding, molding, pressing or the like, to form an endless or continuous band. As shown in FIGS. 10 to 12, the band tapers inwardly toward the gum line or gingival end 41. Thus, the band 40 is funnel like in shape. In accordance with this embodiment of the invention, the height H of the endless band is sized to extend above the surface S of a prepared tooth for which band 40 is designed to encircle. Also, the sides of the band 40 are tapered or sloped inwardly at an angle A ranging between 7 to 12 degrees relative to the vertical as seen in FIG. 10. The arrangement is such that portion H-1 of the matrix extending above the surface of the tooth with an angle of inclination of 7 to 12 degrees together with the 0.2 mm thickness of the band 40 is sufficient to form an optical illusion of a thicker occlusal end to define the outer periphery of the tooth, such that a proper signal is transmitted to the milling portions of the CAD-CAM machine to form the appropriate crown or bridge. Preferably, the height of the portion H-1, which extends above the prepared surface S of the tooth to be restored is in the range of 7 to 10 mm. It will be understood that the original height of the matrix band is of sufficient height so as to enable the dentist to trim the same to suit the particular situation. However, the dentist should allow any such trimmed matrix band to extend at least 7 to 10 mm above the surface of the floor of a prepared tooth to provide for the optical illusion of a thicker occlusal edge. In all other respects, the matrix band 40 is used in a manner as hereinbefore described.

While the invention has been described with respect to the illustrated embodiments, it will be readily understood and appreciated by those skilled in the art that variations and modifications may be made without departing from the spirit or scope of the invention.

What is claimed is:

1. A dental imaging matrix band comprising
an elongated metallic blank of relatively thin flexible sheet material having a height corresponding at least substantially to the height of a tooth extending beyond the gum line,
said blank being sufficiently long and flexible for encircling at least one prepared tooth,
said blank having opposed ends,
means for securing the opposed ends to encircle the prepared tooth,
said band having a buccal and lingual side,
said buccal and lingual sides of said band having a thickness greater than the thickness of said opposed ends interconnecting said thickened buccal and lingual sides.

2. A dental imaging matrix band as defined in claim 1 wherein said metallic blank is non-reflective.

3. A dental imaging matrix band as defined in claim 1 wherein said endless band tapers inwardly toward the gum line.

4. A dental imaging matrix band as defined in claim 1 wherein the thickened buccal and lingual sides of said band simulate the walls of a tooth allowing for a clear optical impression of the floor of the tooth.

5. A dental imaging matrix band comprising
an endless loop adapted to be fitted to a prepared tooth,
said loop having a height at least substantially equal to the height of the tooth extending beyond the gum line,
said loop having a buccal side and a lingual side, and opposed ends interconnected between said buccal side and lingual side,
said buccal and lingual sides having a thickness greater than the opposed ends of said loop whereby the thicker buccal and lingual sides allow for a clear optical impression of the floor of the tooth.

6. A dental imaging matrix band as defined in claim 5 wherein said endless loop tapers inwardly toward the gum line.

7. A dental imaging matrix band comprising
a metallic band adapted to circumscribe a prepared tooth to be restored,
said band having a height at least as great as the height of a prepared tooth to be restored,
said band being tapered inwardly toward the gingival end of the band,
said band being formed of a non-reflective metal,
and means formed integral with said band to simulate a clear optical image of the floor of the prepared tooth.

8. A dental imaging matrix band as defined in claim 7 wherein said matrix band includes opposed buccal and lingual sides and opposed end interconnected between said buccal and lingual sides, said buccal and lingual sides having a thickness greater than that of said opposed ends, said thicker buccal and lingual sides being formed on the exterior surface of said matrix band whereby the thicker buccal and lingual sides define an optical image simulating the circumference of the prepared tooth allowing for a clear optical impression of the prepared tooth.

9. A dental imaging matrix band as defined in claim 7 wherein the gingival end of said matrix band has a diameter of approximately 6 mm and the occlusal end diameter of approximately 13 mm.

10. A dental imaging matrix band as defined in claim 7 wherein said metallic band is formed of a uniform thickness, and said band having a portion which extends beyond the surface of a prepared tooth adapted to receive said band, said portion of the band extending above the surface of a prepared tooth being coincident with the taper of said band, whereby the extended portion of said band in conjunction with the uniform thickness of said band creates an optical illusion of a thickened occlusal end which enables the optical scanner of a CAD-CAM machine to image the periphery of the tooth.

11. A dental imaging matrix band as defined in claim 10 wherein the uniform thickness of the band is approximately 0.2 mm.

12. A dental imaging matrix band as defined in claim 10 wherein the taper of said band defines an angle ranging between 7 to 12 degrees.

13. A dental imaging matrix band as defined in claim 10 in which the portion of the band extending beyond the surface of a prepared tooth ranges between 7 to 10 mm.

14. A dental imaging matrix band comprising a band of non-reflective metal adapted to circumscribe at least one tooth to be restored, said band being formed of a uniform thickness, and said band having a height which extends beyond the surface of a prepared tooth adapted to receive said band, said extending portion of said band tapering outwardly toward the occlusal end of said band at an angle ranging between 7 to 12 degrees wherein the uniform thickness of said band and extended outwardly tapering of said extended portion creates an optical illusion of a thicker occlusal end which enables an optical scanner of a CAD-CAM machine to image the periphery of the tooth to allow for a clear optical impression of the floor of a prepared tooth.

15. A dental imaging matrix band as defined in claim 14 wherein the uniform thickness of said band is approximately 0.2 mm.

16. A dental imaging matrix band as defined in claim 15 wherein the height of the portion of the band extending beyond the prepared surface of the tooth ranges between 7 to 10 mm.

* * * * *